United States Patent
Ishii et al.

(10) Patent No.: US 10,751,022 B2
(45) Date of Patent: Aug. 25, 2020

(54) RADIATION IMAGE CAPTURING APPARATUS AND RADIATION IMAGE CAPTURING SYSTEM, AND CONTROL METHODS THEREFOR

(71) Applicant: CANON KABUSHIKI KAISHA, Tokyo (JP)

(72) Inventors: Yoshiaki Ishii, Kawasaki (JP); Tomoyuki Yagi, Chofu (JP); Katsuro Takenaka, Honjo (JP); Takuya Ryu, Kokubunji (JP)

(73) Assignee: Canon Kabushiki Kaisha, Tokyo (JP)

( * ) Notice: Subject to any disclaimer, the term of this patent is extended or adjusted under 35 U.S.C. 154(b) by 267 days.

(21) Appl. No.: 15/646,949

(22) Filed: Jul. 11, 2017

(65) Prior Publication Data

US 2018/0021004 A1     Jan. 25, 2018

(30) Foreign Application Priority Data

Jul. 22, 2016    (JP) ................................ 2016-144511

(51) Int. Cl.
*A61B 6/00*       (2006.01)
(52) U.S. Cl.
CPC .............. *A61B 6/54* (2013.01); *A61B 6/4233* (2013.01)
(58) Field of Classification Search
CPC ................................ A61B 6/54; A61B 6/4233
See application file for complete search history.

(56) References Cited

U.S. PATENT DOCUMENTS

| 4,689,487 | A | * | 8/1987 | Nishiki | ................. | G01T 1/2018 |
|---|---|---|---|---|---|---|
| | | | | | | 250/361 R |
| 6,285,738 | B1 | * | 9/2001 | Nagai | ................. | A61B 6/4225 |
| | | | | | | 348/E5.087 |
| 2003/0169847 | A1 | * | 9/2003 | Karellas | ................. | A61B 6/482 |
| | | | | | | 378/98.3 |
| 2011/0024641 | A1 | * | 2/2011 | Yokoyama | ............... | A61B 6/06 |
| | | | | | | 250/370.08 |
| 2011/0128359 | A1 | * | 6/2011 | Yokoyama | ............... | A61B 6/00 |
| | | | | | | 348/61 |

(Continued)

FOREIGN PATENT DOCUMENTS

| CN | 102480601 A | 5/2012 |
|---|---|---|
| CN | 102481130 A | 5/2012 |

(Continued)

*Primary Examiner* — Christine S. Kim
(74) *Attorney, Agent, or Firm* — Canon U.S.A., Inc., IP Division (57) ABSTRACT

A control unit controls a detector including a pixel array arranged in a matrix, a driving circuit that drives the pixel array by a changeable number of pixels, and a readout circuit that outputs an electrical signal from the pixel array. The control unit controls, with a change from a first image capturing operation for repeating a set of a first accumulation operation and a first image output operation a plurality of times at a first frame rate to a second image capturing operation for repeating a set of a second accumulation operation and a second image output operation a plurality of times at a second frame rate, so that the detector continuously repeats a set of the second accumulation operation and an initialization operation a plurality of times at the second frame rate in a period between the first image capturing operation and the second image capturing operation.

11 Claims, 8 Drawing Sheets

(56) References Cited

U.S. PATENT DOCUMENTS

2012/0170827 A1* 7/2012 Yagi .................... G01T 1/17
                                                          382/132
2018/0350112 A1* 12/2018 Wang .................. A61B 6/025

FOREIGN PATENT DOCUMENTS

| CN | 102498713 A | 6/2012 |
| CN | 102551767 A | 7/2012 |
| CN | 103369256 A | 10/2013 |
| JP | H09021879 A | 1/1997 |
| JP | 2010-246835 A | 11/2010 |
| JP | 2011-066514 A | 3/2011 |
| JP | 2014-030216 A | 2/2014 |
| JP | 2016-010064 A | 1/2016 |

* cited by examiner

RADIATION IMAGE CAPTURING APPARATUS AND RADIATION IMAGE CAPTURING SYSTEM, AND CONTROL METHODS THEREFOR

BACKGROUND OF THE INVENTION

Field of Invention

The present invention relates to an image capturing apparatus and an image capturing system, a control method therefor, and a storage medium storing a control program therefor. More specifically, the present invention relates to a radiation image capturing apparatus and a radiation image capturing system preferably used for still image capturing such as radiography and moving image capturing such as fluorography in medical diagnosis, control methods therefor, and a storage medium storing a program therefor.

Description of Related Art

In recent years, as an image capturing apparatus used for X-ray medical image diagnosis and non-destructive inspection, a radiation image capturing apparatus using a flat panel detector (hereinafter, referred to as FPD) formed of a semiconductor material has started to be put into practical use. This radiation image capturing apparatus has been used as a radiation image capturing apparatus for acquiring a digital radiation image by still image capturing such as radiography and moving image capturing such as fluorography in medial image diagnosis, for example.

In such a radiation image capturing apparatus, it has been examined that a plurality of image capturing operations is switched depending on a use case for image capturing to match various use cases, as discussed in Japanese Patent Application Laid-Open No. 2010-246835 and Japanese Patent Application Laid-Open No. 2011-066514.

However, when a parameter (e.g., a frame rate, a gain, or a number of pixels to be added) for an image capturing operation differs before and after a change, an artifact may occur in an image acquired after the change depending on the difference thereof. An artifact may occur not only when the image capturing operation shifts from radiography to fluorography but also when the image capturing operation shifts from fluorography to fluorography having a different parameter, i.e., between moving image capturing and moving image capturing which are respectively controlled by different parameters for the image capturing operation. The artifact may reduce the quality of an image acquired after the change. In addition, as the number of image capturing operations respectively having different parameters increases, the image capturing operations are not easily dealt with individually by image processing. Therefore, it is desirable that the above-described issue can be solved by simple processing.

SUMMARY OF THE INVENTION

The present invention is directed to a radiation image capturing apparatus capable of reducing an artifact caused by a change between image capturing operations respectively having different parameters by being controlled without performing complicated image processing.

According to an aspect of the present invention, an image capturing apparatus includes a detector including a pixel array having a plurality of pixels arranged in a matrix, each pixel including a conversion element for converting radiation or light into an electrical signal, a driving circuit configured to drive the pixel array by a changeable number of pixels to be added, and a readout circuit configured to amplify and output the electrical signal from the driven pixel array, and a control unit configured to control the driving circuit and the readout circuit, wherein the control unit controls, with a change from a first image capturing operation for continuously repeating a set of a first accumulation operation for accumulating an electrical signal in the pixel during a first time period and a first image output operation for amplifying the electrical signal accumulated in the pixel by the first accumulation operation and output from the pixel array driven by a first number of pixels to be added using a first amplification factor of the readout circuit as an amplification factor and outputting the amplified electrical signal as image data a plurality of times at a first frame rate, to a second image capturing operation for continuously repeating a set of a second accumulation operation for accumulating the electrical signal in the pixel during a second time period different in length from the first time period and a second image output operation for amplifying the electrical signal accumulated in the pixel by the second accumulation operation and output from the pixel array driven by a second number of pixels to be added different from the first number of pixels to be added using a second amplification factor of the readout circuit as an amplification factor different from the first amplification factor and outputting the amplified electrical signal as image data a plurality of times at a second frame rate different from the first frame rate, the driving circuit and the readout circuit so that the detector repeats a set of the second accumulation operation and an initialization operation for initializing the conversion element by the pixel array being driven by the second number of pixels to be added and using the second amplification factor of the readout circuit as the amplification factor a plurality of times at the second frame rate in a period between the first image capturing operation and the second image capturing operation.

Further features of the present invention will become apparent from the following description of exemplary embodiments with reference to the attached drawings.

DESCRIPTION OF THE EMBODIMENTS

An exemplary embodiment to which the present invention is applicable will be specifically described below with reference to the drawings. In the present exemplary embodiment, radiation includes beams each having a similar degree or more of energy, e.g., an X-ray, a particle beam, and a cosmic ray in addition to an alpha ray, a beta ray, and a gamma ray serving as a beam produced by particles (including photons) emitted by radiation decay.

Figure 1:
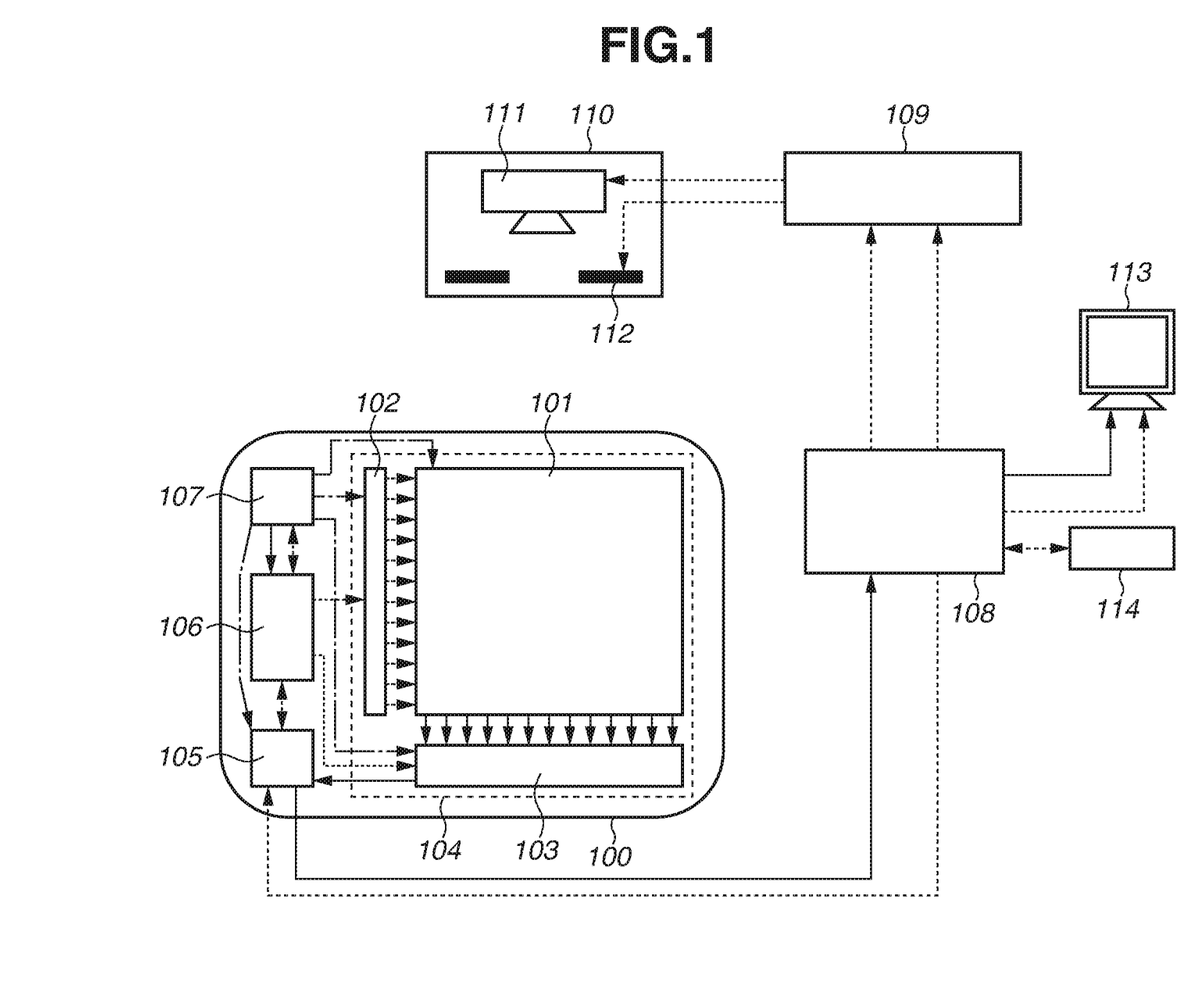
FIG. 1 is a schematic view illustrating a radiation image capturing system.

A radiation image capturing system illustrated in FIG. 1 includes a radiation image capturing apparatus 100, a control computer 108, a radiation control apparatus 109, a radiation generation apparatus 110, a display apparatus 113, and a control console 114. The radiation image capturing apparatus 100 includes a flat panel detector (FPD) 104 including a pixel array 101, a driving circuit 102, and a readout circuit 103. The pixel array 101 has a plurality of pixels arranged therein in a matrix shape for converting radiation or light into electrical signals. The driving circuit 102 drives the pixel array 101 by a changeable number of pixels to be added. The readout circuit 103 amplifies the electrical signal from the driven pixel array 101, and outputs the amplified electrical signal as image data. The radiation image capturing apparatus 100 further includes a signal processing unit 105 configured to process and output the image data from the FPD 104, a control unit 106 for supplying a control signal to each of components and controls an operation of the radiation image capturing apparatus 100, and a power source unit 107 configured to supply a bias to each of the components. The signal processing unit 105 receives the control signal from the control computer 108 (described below) and provides the received control signal to the control unit 106. The control unit 106 controls the driving circuit 102 upon receiving the control signal from the control computer 108 (described below). The driving circuit 102 is configured to enable a scanning region and a number of pixels to be added to be switched upon receiving the control signal from the control unit 106. The power source unit 107 includes a power source circuit such as a regulator configured to supply a voltage required in the pixel array 101, the driving circuit 102, and the readout circuit 103 by receiving a voltage from an external power source or a built-in battery (not illustrated). In the present exemplary embodiment, the control unit 106 has a function of enabling a plurality of image capturing operations to be switched. The image capturing operation in the present exemplary embodiment uses a plurality of parameters, and is determined by a combination of respective values of the parameters previously prepared. The parameters include a frame rate, an amplification factor (gain), and a number of pixels to be added (binning). The number of pixels to be added corresponds to a number of pixel rows simultaneously driven by the driving circuit 102. For example, the number of pixels to be added is one if the number of pixel rows simultaneously driven is only one, and is two if the number of pixel rows simultaneously driven is two. Pixel-binning is used in flat-panel (FP) x-ray detectors for fluoroscopy to increase signal-to-noise ratio (SNR) and to decrease digital data transfer rates. Pixel-binning is a mode in which the X-ray detector can run in that it takes a 2×2 matrix of pixels and combines them to effectively create one larger pixel. This is caused by the detector taking a 2×2 pixel matrix and adding the values of detected radiation together. This is done in the hardware internally in the detector so there is no additional processing time for the computer. There are a number of benefits to using pixel binning including better signal level, higher contrast, and faster framerates. Specifically, because pixel binning is done within the hardware of the detector, there is less data to transfer to the computer. This allows the detector to run at much higher frame rates than is possible without pixel binning.

The control computer 108 synchronizes the radiation generation apparatus 110 and the radiation image capturing apparatus 100, transmits a control signal for determining a state of the radiation image capturing apparatus 100, and performs image processing for correction, storage, and display for the image data from the radiation image capturing apparatus 100. The control computer 108 transmits a control signal for determining an irradiation condition of radiation to the radiation control apparatus 109 based on information from the control console 114.

The radiation control apparatus 109 controls an operation for radiating radiation from a radiation source 111 included in the radiation generation apparatus 110 and an operation of an exposure field aperture mechanism 112 by receiving the control signal from the control computer 108. The exposure field aperture mechanism 112 has a function of changing a predetermined exposure field serving as a region where the pixel array 101 in the radiation image capturing apparatus 100 is irradiated with radiation or light corresponding to the radiation. The control console 114 receives input information about a subject and an image capturing condition (including an image capturing operation and an operation mode) as parameters for various types of controls by the control computer 108, and transmits the parameters to the control computer 108. The display apparatus 113 displays image data processed by the control computer 108.

Figure 2A:
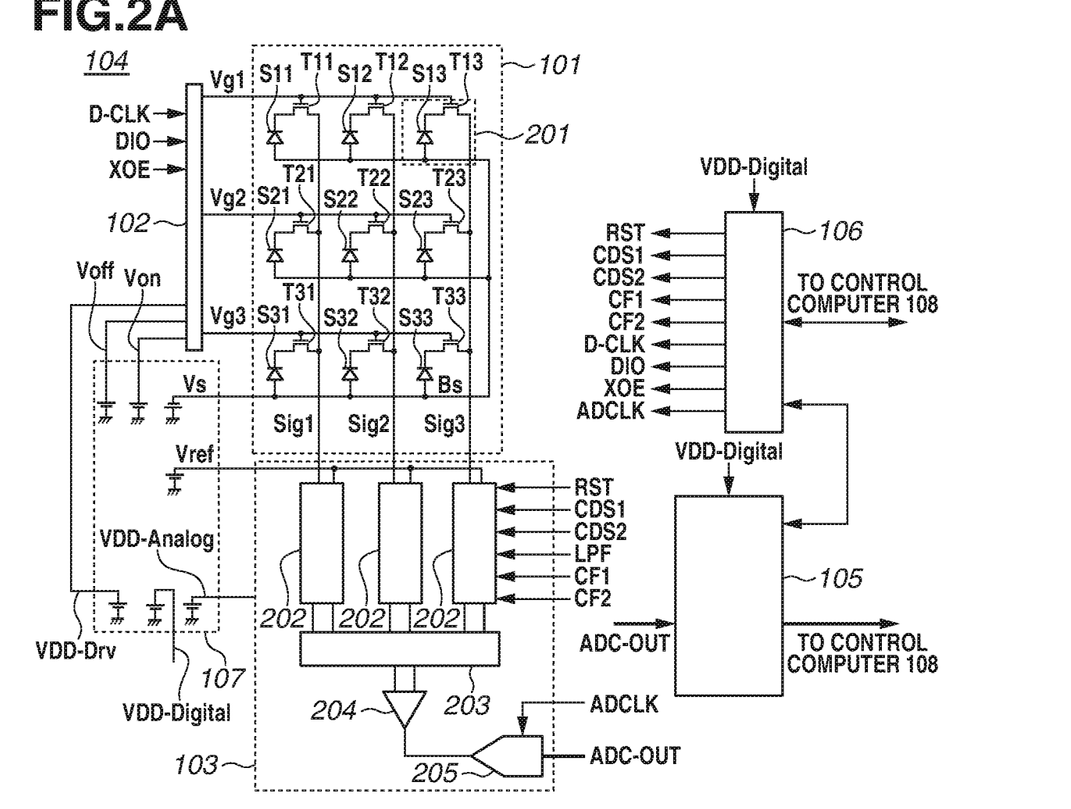
FIGS. 2A and 2B are schematic equivalent circuit diagrams each illustrating a radiation image capturing apparatus.
Figure 2B:
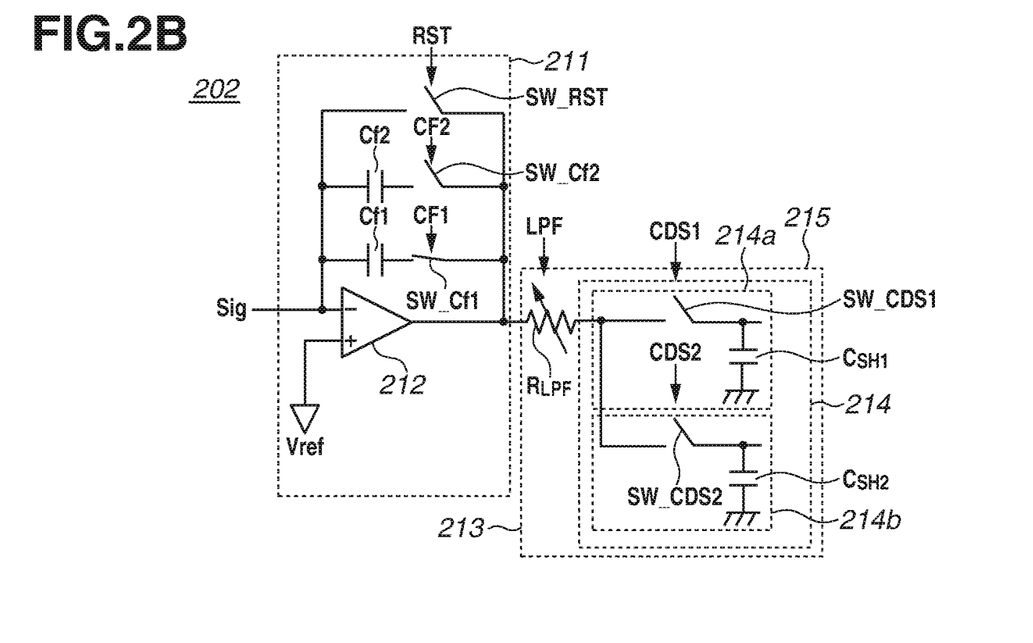

A configuration of the FPD 104 in the radiation image capturing apparatus 100 will be described below with reference to FIGS. 2A and 2B. FIG. 2A is a schematic equivalent circuit diagram illustrating an entire configuration of the FPD 104 in the radiation image capturing apparatus 100, and FIG. 2B is a schematic equivalent circuit diagram illustrating a part of the FPD 104. The same components as those in FIG. 1 are assigned the same reference numbers, and hence detailed description thereof is omitted. FIG. 2 illustrates a radiation image capturing apparatus 100 including an FPD having pixels of 3 rows×3 columns for simplification of description. An actual radiation image capturing apparatus 100 has more pixels. For example, a 17-inch radiation image capturing apparatus 100 has pixels of approximately 2800 rows×approximately 2800 columns.

As illustrated in FIG. 2A, the pixel array 101 has a plurality of pixels 201 arranged in a matrix of rows and columns. The pixels 201 respectively include conversion elements S11 to S33 for converting radiation or light into electrical charges and switch elements T11 to T33 for outputting electrical signals respectively corresponding to the charges. In the present exemplary embodiment, a photoelectric conversion element for converting the light radiated onto each of the conversion elements S11 to S33 into a charge includes a PIN photodiode arranged on an insulating substrate such as a glass substrate and made of amorphous silicon as a main material. Each of the conversion elements S11 to S33 preferably includes an indirect-type conversion element including a wavelength conversion element for converting radiation into light in a wavelength band detectable by the photoelectric conversion element on the radiation incident side of the photoelectric conversion element, and a direct-type conversion element for directly converting radiation into a charge. Each of the switch elements T11 to T33 preferably includes a transistor having a control terminal and two main terminals, and includes a thin film transistor (TFT) in the present exemplary embodiment. Each of the conversion elements S11 to S33 has an electrode electrically connected to one main terminal of the corresponding one of switch elements T11 to T33, and has another electrode electrically connected to the power source unit 107 for supplying a bias voltage Vs via a common bias wiring Bs. The switch elements in a row direction, e.g., T11, T12, and T13 have their respective control terminals electrically connected to a driving wiring Vg1 in the first row. Driving signal for controlling conductive states of the switch elements T11, T12, and T13 are fed to the switch elements T11, T12, and T13 by row basis via the driving wiring Vg1 from the driving circuit 102. In this way, when the driving circuit 102 controls conductive states and non-conductive states of the switch elements T11, T12, and T13 by row basis, the driving circuit 102 scans the pixels 201 by row basis. The scanning region in the present exemplary embodiment is a region where the driving circuit 102 scans the pixels 201 by row basis, as described above. The switch elements in a column direction, e.g., T11, T21, and T31 have their other main terminals electrically connected to a signal wiring Sig1 in the first column, and output electrical signals corresponding to the charges generated by the conversion elements to the readout circuit 103 via the signal wiring Sig1 while the switch elements are conductive. Each of a plurality of signal wirings Sig1 to Sig3 arranged in the column direction transmits the electrical signals output from the plurality of pixels 201 in parallel to the readout circuit 103.

The readout circuit 103 includes column circuits 202 provided for signal wirings (for each column in the pixel array 101), a multiplexer 203, a buffer amplifier 204, and an analog-to-digital converter (A/D converter) 205. A configuration of each of the column circuits 202 will be specifically described below with reference to FIG. 2B. The multiplexer 203 converts parallel analog electrical signals respectively output from the column circuits 202 into a serial analog electrical signal. The buffer amplifier 204 transmits the serial analog electrical signal from the multiplexer 203 to the A/D converter 205. The A/D converter 205 converts the serial analog electrical signal output from the buffer amplifier 204 into a digital signal. The buffer amplifier 204 preferably include a differential amplifier for outputting a differential signal of two electrical signals from any of the column circuits 202 selected by the multiplexer 203. A reference voltage Vref and a power source voltage VDD-Analog are supplied to the column circuit 202 from the power source unit 107.

Digital image data ADC-OUT sent from the A/D converter 205 is input to the signal processing unit 105. The signal processing unit 105 can perform various types of image processing for generating a radiation image, and stores correction data for the processing. The image data processed by the signal processing unit 105 is output to the control computer 108.

The driving circuit 102 feeds the driving signals to the switch elements T11 to T33 via the driving wirings Vg1 to Vg3. When the driving signals have an on voltage Von, the switch elements T11 to T33 are turned on. If the driving signals have an off voltage Voff, the switch elements T11 to T33 are turned off, and the pixels 201 respectively store the charges generated by the conversion elements S11 to S33. The driving circuit 102 switches the voltages of the driving signals fed to the driving wirings Vg1 to Vg3 in response to a control signal (D-CLK, XOE, or DIO) from the control unit 106.

The control unit 106 receives the control signal from the control computer 108 outside the radiation image capturing apparatus 100 via the signal processing unit 105 and feeds various types of control signals to the driving circuit 102, the power source unit 107, and the readout circuit 103, to control an operation of the FPD 104. The control unit 106 feeds the control signal D-CLK, the control signal XOE, and the control signal DIO to the driving circuit 102, to control an operation of the driving circuit 102. In the present exemplary embodiment, the control signal D-CLK is a shift clock for a shift register used as the driving circuit 102, the control signal DIO is a pulse used for transferring the driving signals from the shift register, and the control signal XOE is used to control an output terminal of the shift register. The control unit 106 controls the driving circuit 102 according to the control signals, to make the scanning region switchable. The control unit 106 feeds control signals RST, CDS1, CDS2, LPF, CF1, CF2, and ADCLK to the readout circuit 103, to control an operation of each of components in the readout circuit 103. The control signal RST is used to control an operation of a reset switch of an integrating amplifier 213 (described below) the control signals CDS1 and CDS2 are used to control an operation of a sample-and-hold circuit 214 (described below), and the control signal ADCLK is used to control an operation of the A/D converter 205. The control signal ADCLK may be used to control an operation of the multiplexer 203.

The power source unit 107 supplies a common bias voltage Vs to the other electrodes of the conversion elements via a bias wiring Bs. The power source unit 107 supplies the reference voltage Vref and the power source voltage VDD-Analog to the readout circuit 103. Further, the power source unit 107 supplies a power source voltage VDD-Drv, the on voltage Von, and the off voltage Voff to the driving circuit 102. The power source unit 107 supplies a power source voltage VDD-Digital to the control unit 106.

An example of a configuration of the column circuit 202 illustrated in FIG. 2A will be described below with reference to FIG. 2B. FIG. 2B is a schematic equivalent circuit diagram illustrating the example of the configuration of the column circuit 202. The column circuit 202 includes an integrating amplifier 213, a sample-and-hold circuit 214 (hereinafter, referred to as an SH circuit), and a low-pass filter 215. In the example illustrated in FIG. 2B, the SH circuit 214 and the low-pass filter 215 share the same circuit element.

The integrating amplifier 213 has the circuit elements illustrated in FIG. 2B. The signal wiring Sig is connected to an inversion input terminal of the operational amplifier 212, and the reference voltage Vref is supplied to a non-inversion input terminal of the operational amplifier 212 from the power source unit 107. Capacitive elements Cf1 and Cf2 are connected in parallel between the inversion input terminal and an output terminal of the operational amplifier 212, respectively, via reset switches SW Cf1 and SW Cf2. The reset switches SW Cf1 and SW Cf2 are respectively controlled to be turned on and off according to the control signals CF1 and CF2 fed from the control unit 106. The control unit 106 switches on and off of each of the reset switches SW Cf1 and SW Cf2, to switch a gain of the integrating amplifier 213.

A reset switch SW RST is further connected in parallel with the capacitive elements Cf1 and Cf2 between the inversion input terminal and the output terminal of the operational amplifier 212. The reset switch SW RST is controlled to be turned on and off according to the control signal RST fed from the control unit 106. When the reset switch SW RST is turned on, the inversion input terminal and the output terminal of the operational amplifier 212 are short circuited, so that the integrating amplifier 213 is reset.

The SH circuit 214 includes a first SH circuit 214a and a second SH circuit 214b each performing a holding operation of holding an analog signal. The first SH circuit 214a includes a capacitive element $C_{SH1}$ and a reset switch SW_CDS1 connected to one electrode of the capacitive element $C_{SH1}$. The second SH circuit 214b includes a capacitive element $C_{SH2}$ and a reset switch SW_CDS2 connected to one electrode of the capacitive element $C_{SH2}$. The reset switches SW_CDS1 and SW_CDS2 are respectively controlled to be turned on and off according to the control signals CDS1 and CDS2 fed from the control unit 106. When the reset switch SW_CDS1 is switched from off to on, the first SH circuit 214a is switched from a hold mode to a sampling mode. During the sampling mode, the capacitive element $C_{SH1}$ is charged with an input signal to the first SH circuit 214a. When the reset switch SW_CDS1 is switched from on to off, the first SH circuit 214a is switched from a sampling mode to a holding mode. During the holding mode, a signal held in the capacitive element $C_{SH1}$ is held (fixed). The same is true for the second SH circuit 214b. The SH circuit 214 is a sample-and-hold circuit for performing correlated double sampling (CDS). The first SH circuit 214a samples a noise signal after resetting the integrating amplifier 213, and the second SH circuit 214b samples a signal from the pixel 201, i.e., a pixel signal. Both the signals are subjected to differential processing by the differential amplifier used as the buffer amplifier 204, and an obtained signal is then fed to the A/D converter 205 after its noise signal component has been removed therefrom.

A variable resistive element $R_{LPF}$ is connected between the integrating amplifier 213 and the SH circuit 214. The variable resistive element $R_{LPF}$ changes its own resistance value in response to the control signal LPF fed from the control unit 106. When the reset switch SW_CDS1 is turned on, the variable resistive element $R_{LPF}$ and the capacitive element $C_{SH1}$ is short-circuited, and the variable resistive element $R_{LPF}$ and the capacitive element $C_{SH1}$ form a low-pass filter. The low-pass filter is a filter circuit for filtering a signal obtained from the integrating amplifier 213. The signal filtered by the low-pass filter is held in the capacitive element $C_{SH1}$. When the reset switch SW_CDS1 is turned off in this state, a voltage signal held in the capacitive element $C_{SH1}$ is held, and is then fed to the multiplexer 203. If the reset switch SW_CDS2 is turned on, a voltage signal is similarly held in the capacitive element $C_{SH2}$, and is then fed to the multiplexer 203.

Figure 3:
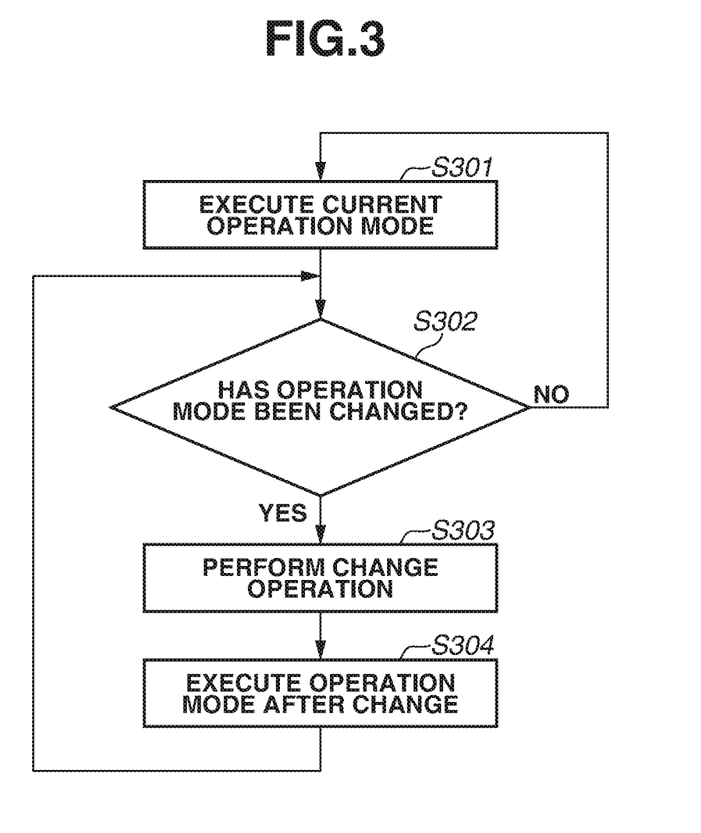
FIG. 3 is a flowchart illustrating respective operations of the radiation image capturing system and the radiation image capturing apparatus.
Figure 4:
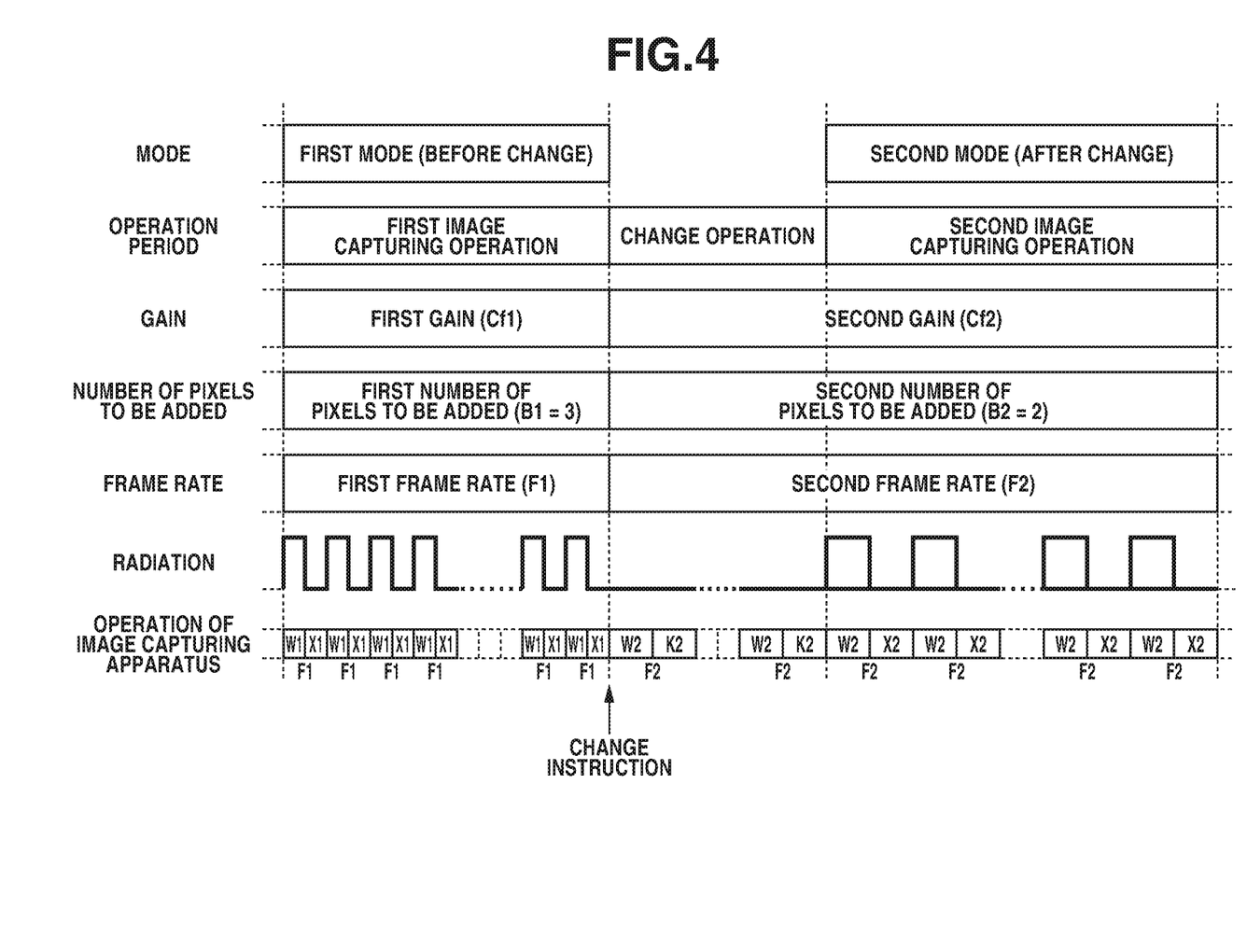
FIG. 4 is a timing chart illustrating an operation of the radiation image capturing apparatus.

Operations of the radiation image capturing system and the radiation image capturing apparatus 100 will be described below with reference to FIGS. 3 and 4. FIG. 3 is a flowchart illustrating the operations of the radiation image capturing system and the radiation image capturing apparatus 100, and FIG. 4 is a timing chart illustrating the operation of the radiation image capturing apparatus 100. In step S301 illustrated in FIG. 3, the radiation image capturing apparatus 100 performs an image capturing operation in an operation mode already set. In this case, the radiation image capturing apparatus 100 performs a first image capturing operation according to a first mode serving as a current operation mode, as illustrated in FIG. 4. In FIG. 4, a moving image capturing operation for repeating a set of a first accumulation operation W1 and a first image output operation X1 a plurality of times is performed as the first image capturing operation. In the first mode, the gain of the integrating amplifier 213 is set to a first gain (first amplification factor) Cf1 defined by the capacitance Cf1 by the control signal CF1. The number of pixels to be added and the frame rate are respectively set to a first number of pixels to be added B1 (=3) and a first frame rate F1 defined by the control signals D-CLK, DIO, and XOE. Details of the accumulation operation and the image output operation will be described below.

In step S302 illustrated in FIG. 3, the control computer 108 determines whether the operation mode has been changed. If the operation mode has not been changed (NO in step S302), the processing returns to step S301 to continue the current operation mode. When an operator instructs the control computer 108 to change the operation mode via the control console 114, a change instruction to request the change of the operation mode is sent from the control computer 108 to the control unit 106 in the radiation image capturing apparatus 100. Parameters changed from the first mode to a second mode include a gain (from Cf1 to Cf2) of the integrating amplifier 213, a number of pixels to be added (from B1 to B2), and a frame rate (from F1 to F2). Other parameters include a time period required for an accumulation operation and a time period required to scan the pixel array 101 in the image output operation by the driving circuit 102. If the operation mode (the second mode illustrated in FIG. 4) set via the control console 114 by the operator has been changed from the current operation mode (the first mode illustrated in FIG. 4) (YES in step S302), then in step S303, the radiation image capturing apparatus 100 performs a change operation to switch the operation mode. The change operation is an operation for stabilizing respective variations in an artifact or an offset component caused by the switching of the operation mode. As illustrated in FIG. 4, the radiation image capturing apparatus 100 is performing an operation for repeating a set of a second accumulation operation W2 and an initialization operation K2 a plurality of times as the change operation. In the change operation, the gain of the integrating amplifier 213 is set to a second gain (second amplification factor) Cf2 defined by the capacitance Cf2 according to the control signal CF2. The number of pixels to be added and the frame rate are respectively set to a second number of pixels to be added B2 (=2) and a second frame rate F2 defined by the control signals D-CLK, DIO, and XOE. More specifically, the gain of the integrating amplifier 213, the number of pixels to be added, and the frame rate in the change operation are respectively changed to match a gain of the integrating amplifier 213, a number of pixels to be added, and a frame rate in the second image capturing operation after the change. A time period required for the second accumulation operation W2 and a time period required to scan the pixel array 101 in the change operation are changed to match a time period required for a second accumulation operation W2 and a time period required to scan the pixel array 101 in the second image capturing operation after the change. All parameters in the change operation are more preferably equal to parameters in the second image capturing operation after the change. Details of the initialization operation K2 will be described below.

In step S304 illustrated in FIG. 3, the operator executes an operation mode set via the control console 114 by the operator, e.g., a moving image capturing operation such as fluoroscopy. More specifically, the control unit 106 performs a moving image capturing operation (the second image capturing operation illustrated in FIG. 4) according to each of the set parameters. In FIG. 4, a moving image capturing operation for repeating the second accumulation operation W2 and a second image output operation X2 a plurality of times is performed as the second image capturing operation. In the second mode, the gain of the integrating amplifier 213 is set to a second gain Cf2 defined by the capacitance Cf2 according to the control signal CF2. The number of pixels to be added and the frame rate are respectively set to a second number of pixels to be added B2 (=2) and a second frame rate F2 defined by the control signals D-CLK, DIO, and XOE. In the moving image capturing operation, radiation is intermittently radiated from the radiation generation apparatus 110, and the radiation image capturing apparatus 100 performs an image capturing operation corresponding to a plurality of frames in synchronization with the emission of the radiation. The moving image capturing operation can end at any time. The operation mode can also be changed during the moving image capturing operation. If the moving image capturing operation ends, the intermittent emission of the radiation from the radiation generation apparatus 110 is stopped, and the radiation image capturing apparatus 100 stops the image capturing operation. When the operator instructs the control computer 108 to change the operation mode via the control console 114, a change instruction to request the change of the operation mode can be sent from the control computer 108 to the control unit 106 in the radiation image capturing apparatus 100. In step S304, the control unit 106 changes the operation mode to an operation mode corresponding to the received change instruction. When the operator instructs the control computer 108 to change the operation mode via the control console 114, an instruction to temporarily stop generating the radiation by the radiation generation apparatus 110 is sent to the radiation control apparatus 109, to temporarily stop generating the radiation. When the operation mode of the radiation image capturing apparatus 100 has been changed, and the moving image capturing operation becomes able to resume, the control computer 108 sends an instruction to start emitting the radiation by the radiation generation apparatus 110 to the radiation control apparatus 109. If the control unit 106 receives an instruction to change the operation mode when the readout circuit 103 is reading out an image of a frame, the control unit 106 changes the operation mode after an image output operation for reading out the image in the frame ends.

Figure 5:
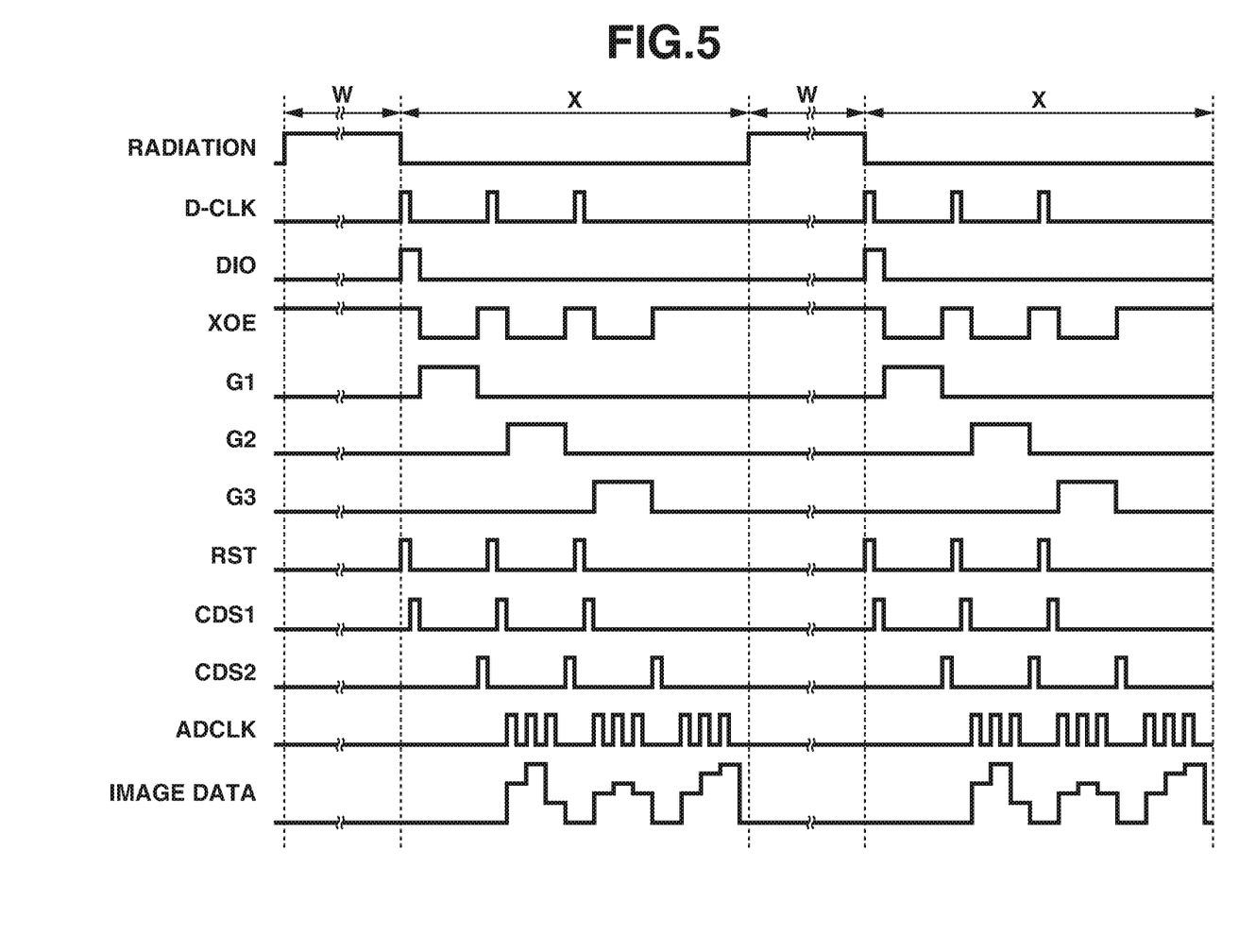
FIG. 5 is a timing chart illustrating an operation of the radiation image capturing apparatus.
Figure 6:
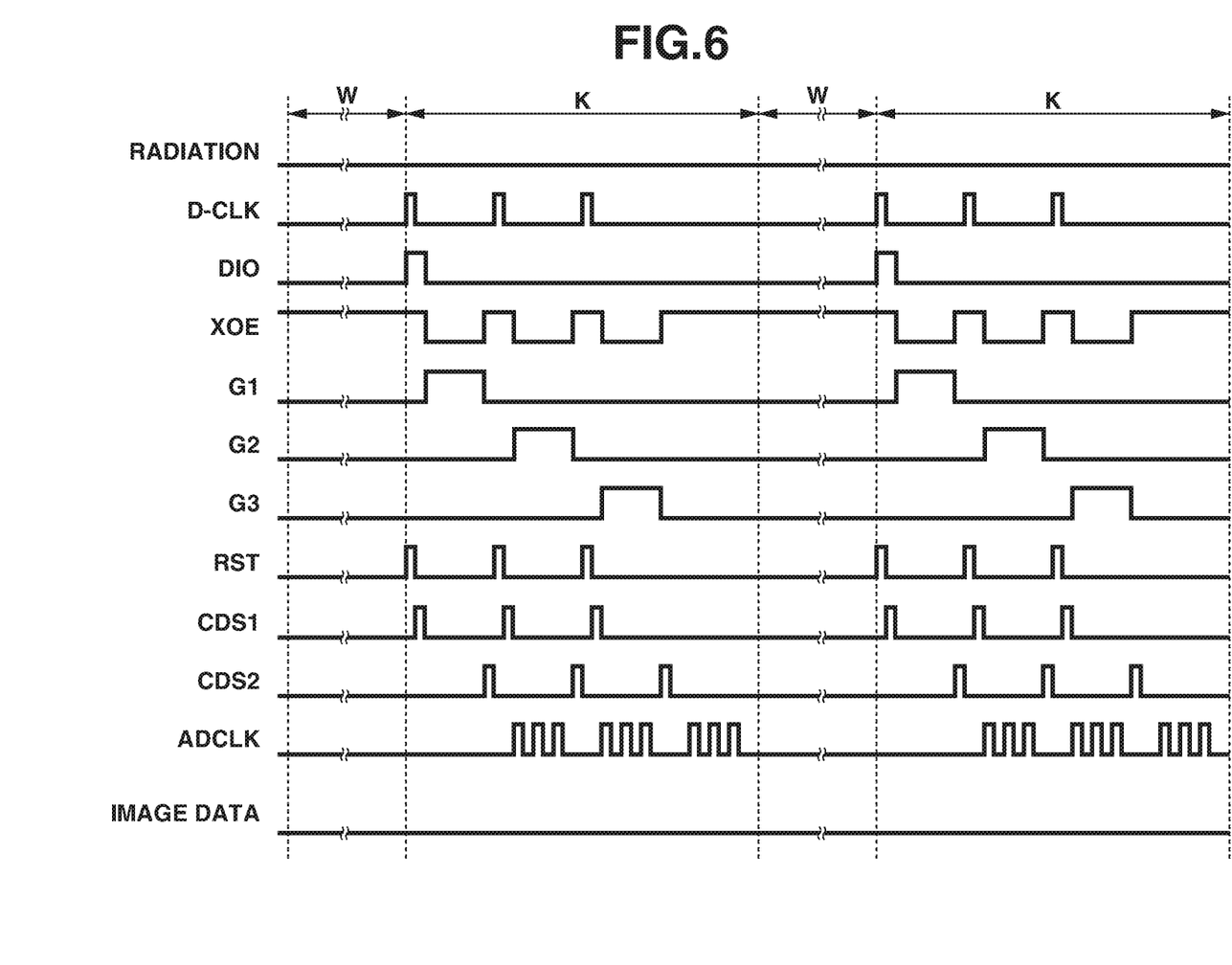
FIG. 6 is a timing chart illustrating an operation of the radiation image capturing apparatus.

Each accumulation operation, each image output operation, and an initialization operation will be described below with reference to FIGS. 5 and 6. FIG. 5 is a timing chart illustrating each accumulation operation and each image output operation, and FIG. 6 is a timing chart illustrating each accumulation operation and an initialization operation. Driving signals G1 to G3 are respectively fed to the driving wirings Vg1 to Vg3 from the driving circuit 102, and each of the driving signals includes a conductive voltage and a non-conductive voltage. Image data illustrated in FIGS. 5 and 6 are respectively image data stored in a memory of the signal processing unit 105.

As illustrated in FIGS. 5 and 6, in each accumulation operation W, the non-conductive voltage is applied to each of the switch elements T11 to T33 in all the pixels 201 while the bias voltage Vs is applied to the conversion elements S11 to S33 in all the pixels 201 so that the switch elements T11 to T33 in all the pixels 201 are set to be non-conductive. In this way, an electrical signal can be accumulated in each of all the pixels 201 in the pixel array 101. If the pixel array 101 is irradiated with radiation in a period during which the switch elements T11 to T33 in all the pixels 201 are set to be non-conductive, as illustrated in FIG. 5, an accumulation operation for accumulating charges respectively generated by the conversion elements S11 to S33 in response to the irradiated radiation is performed. On the other hand, if the pixel array 101 is not irradiated with radiation in a period during which the switch elements T11 to T33 in all the pixels 201 are set to be non-conductive, as illustrated in FIG. 6, an accumulation operation for accumulating dark-time charges generated regardless of the emission of the radiation by the conversion elements S11 to S33 is performed. The first accumulation operation W1 is intended to be an accumulation operation in the first image capturing operation, and the second accumulation operation W2 is intended to be an accumulation operation in the second image capturing operation. Since the accumulation operation in the change operation is the second accumulation operation W2, it is intended that the second accumulation operation W2 in the change operation is performed in the same time period as that during which the second accumulation operation W2 in the second image capturing operation is performed.

Next, as illustrated in FIG. 5, in each image output operation X, the capacitance of the integrating amplifier 213 and the signal wirings Sig are first reset in response to the control signal RST from the control unit 106. Then, the first SH circuit 214a samples a noise signal after resetting the integrating amplifier 213 in response to the control signal CDS1 from the control unit 106. Then, the conductive voltage is applied to the driving wiring Vg1 from the driving circuit 102, so that the switch elements T11, T12, and T13 in the first row are set to be conductive. With this operation, the electrical signals based on the charges generated by the conversion elements S11, S12, and S13 in the first row are respectively output to the signal wirings Sig. The electrical signals output in parallel via the signal wirings Sig are respectively amplified by the integrating amplifiers 213 in the column circuits 202. The amplified electrical signals are respectively held in parallel in the second SH circuits 214b in the column circuits 202 after the second SH circuits 214b are operated in response to the control signal CDS2. The capacitance of the integrating amplifier 213 and the signal wirings Sig are reset again in response to the control signal RST after the electrical signals are held. After the capacitance of the integrating amplifier 213 and the signal wirings Sig are reset, the conductive voltage is applied to the driving wiring Vg2 in the second row, like in the first row, so that the switch elements T21, T22, and T23 in the second row are set to be conductive. In a period during which the switch elements T21, T22, and T23 in the second row are set to be conductive, the multiplexer 203 sequentially outputs the electrical signals held in the SH circuit 214 in response to the control signal ADCLK. Through this operation, the electrical signals from the pixels 201 in the first row read out in parallel are converted into a serial image signal, and the serial image data is output. The A/D converter 205 converts the serial image signal into image data corresponding to the pixels 201 in the first row and outputs the image data in response to the control signal ADCLK. The image data is stored in the memory of the signal processing unit 105. When the above-described operation is performed in units of rows from the first row to the third row, the image data corresponding to one frame are output from the radiation image capturing apparatus 100. The first image output operation X1 is intended to be an image output operation in the first image capturing operation, and the second image output operation X2 is intended to be an image output operation in the second image capturing operation. The image output operation X is an operation for the driving circuit 102 to scan the pixel array 101 on a row basis to output the image data corresponding to one frame from the pixel array 101 via the readout circuit 103.

As illustrated in FIG. 6, an initialization operation K differs from the image output operation X in that the image data from the A/D converter 205 is not stored in the memory of the signal processing unit 105, and is similar to the image output operation X in the operation itself performed by the FPD 104. In other words, the initialization operation K is an operation for the driving circuit 102 to scan the pixel array 101 on a row basis to initialize each of the conversion elements S11 to S33 in the pixel array 101. The initialization operation K is made similar to the image output operation X in the operation performed by the FPD 104 by each of the control signals from the control unit 106 being made common to make a temperature in the initialization operation X substantially similar to that in the image output operation X. Particularly, in the moving image capturing operation, the image output operation X is performed a plurality of times. Therefore, heat generation amounts of the integrating amplifier 213 and the A/D converter 205 become larger in the moving image capturing operation than those in a still image capturing operation, and a temperature becomes higher in the moving image capturing operation than that in the still image capturing operation as a whole. In such a case, in the initialization operation K, a temperature is also preferably a substantially similar temperature to that in the image output operation X in the moving image capturing operation. The initialization operation K may be performed while the control signals CDS1, CDS2, and ADCLK are maintained at a low level. The initialization operation K2 is intended to be an initialization operation performed in the same time period as that during which the image output operation in the second image capturing operation is performed.

Figure 7:
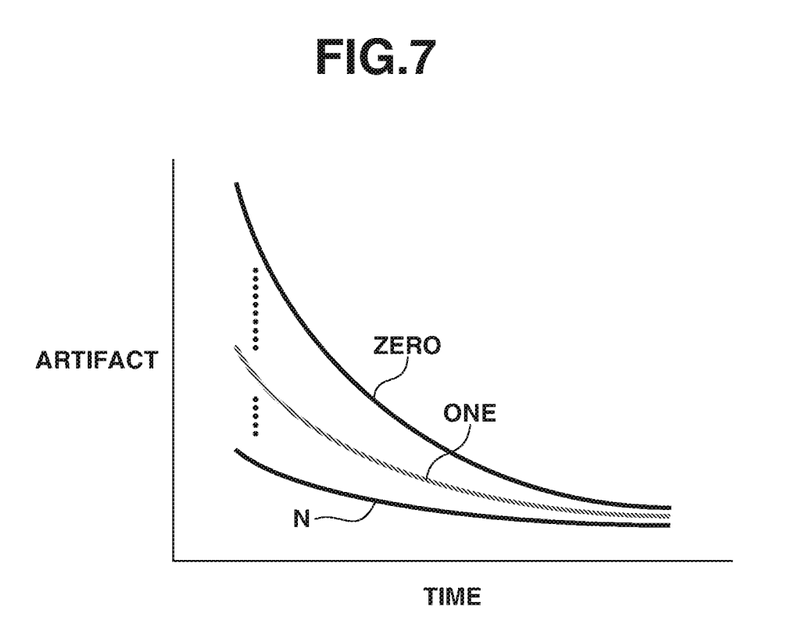
FIG. 7 is a graph illustrating an effect of an exemplary embodiment.

As described above, a change operation is performed to match an operation included in an operation previous to the image output operation in the image capturing operation performed after the change. Accordingly, characteristics of the pixel array 101 and the readout circuit 103 in the second accumulation operation W2 in the image capturing operation are stabilized, so that good image data including a small artifact can be acquired. While the operation for repeating the set of the second accumulation operation W2 and the initialization operation K2 a plurality of times is performed in the change operation illustrated in FIG. 4, the present exemplary embodiment is not limited thereto. The set of the second accumulation operation W2 and the initialization operation K2 may be performed at least once. However, as illustrated in FIG. 7, the larger the number of times the set of the second accumulation operation W2 and the initialization operation K2 is repeated is, the smaller an artifact in an image obtained by the second image capturing operation W2 becomes. FIG. 7 is a graph illustrating a time period elapsed since the second image capturing operation W2 is started (the change operation ended) on a horizontal axis and an artifact on a vertical axis of ordinate. As illustrated in FIG. 7, the artifact in the image is reduced when the number of times the set of the second accumulation operation W2 and the initialization operation K2 is performed is one than when the number of times is zero, and is further reduced when the number of times is N 2) than when the number of times is zero. Thus, the set of the second accumulation operation W2 and the initialization operation K2 is desirably performed as many times as possible in a time period allowable until the second image capturing operation W2 is started since the change instruction is received.

The present exemplary embodiment is merely one example, and the present invention is not limited to this. In the present exemplary embodiment, a time period required for the change operation is made constant regardless of a mode after the change operation. In other words, the number of repetitions of the second accumulation operation W2 and the initialization operation K2 is adjusted so that the time period required for the change operation becomes constant. The time period required for the change operation need not be constant but may be specific for each mode. A time period in that case may be determined by a mode before the change or after the change.

Figure 8:
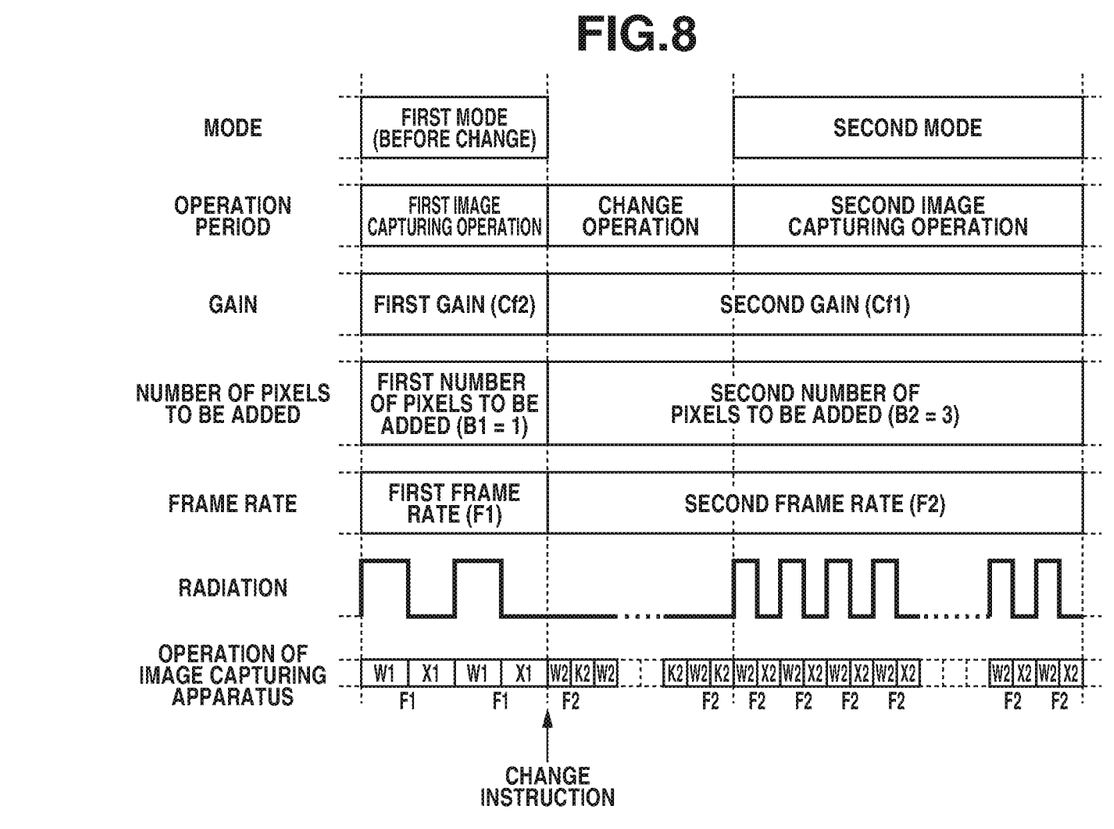
FIG. 8 is a timing chart illustrating another operation of the radiation image capturing apparatus.

As illustrated in FIG. 8, changes of parameters may be the reverse of the changes of the parameters illustrated in FIG. 4. The change is not limited to a change between the moving image capturing operation and the moving image capturing operation. For example, the change may be a change from the still image capturing operation to the moving image capturing operation or a change from the moving image capturing operation to the still image capturing operation. The image capturing operation is not limited to an image capturing operation performed when a subject is captured. For example, the image capturing operation may be an image capturing operation performed during calibration (updating of a gain correction image) or an image capturing operation performed when an offset image is updated.

The present invention can also be implemented by a computer included in the control unit 106 executing a program, for example. Means for supplying the program to the computer, e.g., a computer readable recording medium such as a compact disc read only memory (CD-ROM) recording the program or a transmission medium such as the Internet through which the program is transmitted is also applicable as an exemplary embodiment of the present invention. The above-described program is also applicable as an exemplary embodiment of the present invention. The program, the recording medium, the transmission medium, and a program product are included in the category of the present invention. An exemplary embodiment based on a combination easily conceivable from the present exemplary embodiment is also included in the category of the present invention.

The exemplary embodiments described above enables an artifact caused by a change between image capturing operations respectively having different parameters to be reduced by controlling a radiation image capturing apparatus without performing complicated image processing.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-144511, filed Jul. 22, 2016, which is hereby incorporated by reference herein in its entirety.

What is claimed is:

1. An image capturing apparatus comprising:
a detector including a pixel array having a plurality of pixels arranged in a matrix, each pixel including a conversion element for converting radiation or light into an electrical signal, a driving circuit configured to drive the pixel array by a changeable number of pixels to be added, and a readout circuit configured to amplify and output the electrical signal from the driven pixel array; and
a control unit configured to control the driving circuit and the readout circuit,
wherein the control unit controls, with a change from a first image capturing operation for continuously repeating a set of a first accumulation operation for accumulating an electrical signal in the pixel during a first time period and a first image output operation for amplifying the electrical signal accumulated in the pixel by the first accumulation operation and output from the pixel array of the plurality of pixels simultaneously driven by a first number of pixels to be added using a first amplification factor of the readout circuit as an amplification factor and outputting the amplified electrical signal as image data a plurality of times at a first frame rate, to a second image capturing operation for continuously repeating a set of a second accumulation operation for accumulating the electrical signal in the pixel during a second time period different in length from the first time period and a second image output operation for amplifying the electrical signal accumulated in the pixel by the second accumulation operation and output from the pixel array of the plurality of pixels simultaneously driven by a second number of pixels to be added different from the first number of pixels to be added using a second amplification factor of the readout circuit as an amplification factor different from the first amplification factor and outputting the amplified electrical signal as image data a plurality of times at a second frame rate different from the first frame rate, the driving circuit and the readout circuit so that the detector repeats a set of the second accumulation operation and an initialization operation for initializing the conversion element by the pixel array being driven by the second number of pixels to be added and using the second amplification factor of the readout circuit as the amplification factor a plurality of times at the second frame rate in a period between the first image capturing operation and the second image capturing operation.

2. The image capturing apparatus according to claim 1, wherein the control unit controls the driving circuit and the readout circuit so that the detector performs a change operation for continuously repeating the set of the second accumulation operation and the initialization operation a plurality of times in response to an instruction requesting the change from the first image capturing operation to the second image capturing operation.

3. The image capturing apparatus according to claim 1, wherein the readout circuit includes column circuits respectively provided for columns of the pixel array, a multiplexer configured to convert parallel analog electrical signals respectively output from the column circuits into a serial analog electrical signal, and an analog-to-digital converter configured to convert the serial analog electrical signal into image data, and
wherein the control unit feeds a common control signal to the readout circuit in the initialization operation and the second image capturing operation.

4. The image capturing apparatus according to claim 3, wherein the column circuit includes an integrating amplifier, and
wherein the amplification factor of the readout circuit is defined by an amplification factor of the integrating amplifier.

5. The image capturing apparatus according to claim 4, wherein each pixel includes a switch element configured to output the electrical signal,
wherein the integrating amplifier includes an operational amplifier having an inversion input terminal to which the electrical signal is input, a non-inversion input terminal to which a reference voltage is supplied, and an output terminal, a capacitive element connected between the inversion input terminal and the output terminal, and a reset switch connected between the inversion input terminal and the output terminal in parallel with the capacitive element, and
wherein the control unit controls the driving circuit and the reset switch in the period to cause the detector to perform the initialization operation.

6. The image capturing apparatus according to claim 1, further comprising a signal processing unit configured to process the image data,
wherein the signal processing unit includes a memory configured to store the image data, and
wherein the image data from the detector is not stored in the memory in the initialization operation.

7. The image capturing apparatus according to claim 1, wherein the conversion element includes a photoelectric conversion element for converting light into charge, and a wavelength conversion member for converting radiation into light which can be detected by the photoelectric conversion element.

8. The image capturing apparatus according to claim 7, wherein the photoelectric conversion element includes a PIN photodiode.

9. A radiation image capturing system comprising:
the image capturing apparatus according to claim 1;
a radiation generation apparatus configured to irradiate the image capturing apparatus with the radiation; and
a control apparatus configured to control the image capturing apparatus and the radiation generation apparatus.

10. A method for controlling an image capturing apparatus comprising a detector including a pixel array having a plurality of pixels arranged in a matrix, each pixel including a conversion element for converting radiation or light into an electrical signal, a driving circuit configured to drive the pixel array by a changeable number of pixels to be added, and a readout circuit configured to amplify and output the electrical signal from the driven pixel array, the method comprising:
performing a first image capturing operation for continuously repeating a set of a first accumulation operation for accumulating an electrical signal in the pixel during a first time period and a first image output operation for amplifying the electrical signal accumulated in the pixel by the first accumulating operation and output from the pixel array of the plurality of pixels simultaneously driven by a first number of pixels to be added using a first amplification factor of the readout circuit as an amplification factor and outputting the amplified electrical signal as image data a plurality of times at a first frame rate;

performing a second image capturing operation for continuously repeating a set of a second accumulation operation for accumulating the electrical signal in the pixel during a second time period different from the first time period and a second image output operation for amplifying the electrical signal accumulated in the pixel by the second accumulating operation and output from the pixel array of the plurality of pixels simultaneously driven by a second number of pixels to be added using a second amplification factor of the readout circuit as an amplification factor and outputting the amplified electrical signal as image data a plurality of times at a second frame rate different from the first frame rate; and repeating by the detector, with a change from the first image capturing operation to the second image capturing operation, a set of the second accumulation operation and an initialization operation for initializing the conversion element by the pixel array being driven by the second number of pixels to be added and using the second amplification factor of the readout circuit as the amplification factor a plurality of times at the second frame rate in a period between the first image capturing operation and the second image capturing operation.

11. An image capturing apparatus comprising:

a detector including a pixel array having a plurality of pixels arranged in a matrix, each pixel including a photodiode and including a conversion element for converting radiation or light into an electrical signal, a driving circuit configured to drive the pixel array by a changeable number of pixels to be added, and a readout circuit configured to output the electrical signal from the driven pixel array; and a control unit configured to control the driving circuit and the readout circuit, wherein the control unit controls, with a change from a first image capturing operation for performing a first image output operation for outputting an electrical signal accumulated in the pixel by an accumulation operation and output from the pixel array of the plurality of pixels simultaneously driven by a first number of pixels to be added as image data, to a second image capturing operation for performing a second image output operation for outputting the electrical signal accumulated in the pixel by an accumulation operation and output from the pixel array of the plurality of pixels simultaneously driven by a second number of pixels to be added different from the first number of pixels to be added as image data, the driving circuit and the readout circuit so that the detector performs an initialization operation for initializing the conversion element by the pixel array being driven by the second number of pixels to be added in a period between the first image capturing operation and the second image capturing operation.

* * * * *